(12) United States Patent
Christensen et al.

(10) Patent No.: US 9,610,059 B2
(45) Date of Patent: Apr. 4, 2017

(54) MONITORING SYSTEM FOR MONITORING HEART SIGNALS

(71) Applicant: Acarix A/S, Kgs Lyngby (DK)

(72) Inventors: Claus Bo Voge Christensen, Snekkersten (DK); Weimin Rong, Bagsvaerd (DK)

(73) Assignee: Acarix A/S, Kgs Lyngby (DK)

( * ) Notice: Subject to any disclaimer, the term of this patent is extended or adjusted under 35 U.S.C. 154(b) by 10 days.

(21) Appl. No.: 14/408,953

(22) PCT Filed: Jun. 17, 2013

(86) PCT No.: PCT/EP2013/062467
§ 371 (c)(1),
(2) Date: Dec. 17, 2014

(87) PCT Pub. No.: WO2013/189866
PCT Pub. Date: Dec. 27, 2013

(65) Prior Publication Data
US 2015/0190109 A1 Jul. 9, 2015

Related U.S. Application Data

(60) Provisional application No. 61/660,883, filed on Jun. 18, 2012.

(30) Foreign Application Priority Data

Jun. 18, 2012 (SE) .................................. 1250640-8

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/0004* (2013.01); *A61B 5/02028* (2013.01);
(Continued)

(58) Field of Classification Search
CPC ......... A61B 7/04; A61B 7/045; A61B 5/0255; A61B 5/6801; A61B 5/6823; A61B 5/6832;
(Continued)

(56) References Cited

U.S. PATENT DOCUMENTS 4,878,501 A * 11/1989 Shue ........................ A61B 7/04
600/493
5,078,134 A * 1/1992 Heilman .............. A61B 5/6831
600/508

(Continued)

FOREIGN PATENT DOCUMENTS

| CN | 101128984 | 2/2008 |
|---|---|---|
| CN | 102685285 | 9/2012 |

(Continued)

OTHER PUBLICATIONS

International Search Report for PCT/EP2013/062467 dated Aug. 21, 2013, two pages.

*Primary Examiner* — Eugene T Wu
(74) *Attorney, Agent, or Firm* — Fulwider Patton LLP

(57) ABSTRACT

The invention relates to a monitoring system (1) for monitoring acoustic heart signals, comprising a sensor housing (2) comprising a heart sound sensing element (3) adapted to be arranged in connection to a patient's heart to sense heart sounds and to generate a heart sound signal related to the heart sounds; a monitoring unit housing (4) comprising a processing unit (5) adapted to receive said heart sound signal, wherein said monitoring unit housing (4) is separated from said sensor housing (2) and is adapted to be arranged in relation to the patient's upper sternum, wherein the monitoring system (1) further comprises a flexible elongated connector (6) connecting said sensor housing (2) to said monitoring unit housing (4), said connector (6) having a longitudinal extension along a longitudinal axis (7), wherein
(Continued)

said connector (6) is connected to said monitoring unit housing (4) in an angular relationship, and wherein the angle α between said longitudinal axis (7) and a main axis (8) of said monitoring unit housing (4) is within a predetermined interval.

16 Claims, 3 Drawing Sheets

(51) Int. Cl.
*A61B 5/024* (2006.01)
*A61B 5/0404* (2006.01)
*A61B 5/02* (2006.01)
*A61B 5/0255* (2006.01)

(52) U.S. Cl.
CPC ........ *A61B 5/02438* (2013.01); *A61B 5/0404* (2013.01); *A61B 5/6833* (2013.01); *A61B 5/6835* (2013.01); *A61B 5/72* (2013.01); *A61B 5/742* (2013.01); *A61B 5/0255* (2013.01); *A61B 5/6801* (2013.01); *A61B 5/6823* (2013.01); *A61B 2560/0412* (2013.01); *A61B 2562/0204* (2013.01); *A61B 2562/164* (2013.01)

(58) Field of Classification Search
CPC ................ A61B 5/6833; A61B 5/6835; A61B 2562/164
See application file for complete search history.

(56) References Cited

U.S. PATENT DOCUMENTS

| | | | | |
|---|---|---|---|---|
| 5,483,967 | A * | 1/1996 | Ohtake | A61B 5/04085 128/903 |
| 5,737,429 | A * | 4/1998 | Lee | A61B 7/04 381/67 |
| 6,117,077 | A * | 9/2000 | Del Mar | A61B 5/04085 600/300 |
| 6,790,178 | B1 * | 9/2004 | Mault | A61B 5/0011 128/903 |
| 2004/0267148 | A1 | 12/2004 | Arand | |
| 2006/0030781 | A1 * | 2/2006 | Shennib | A61B 5/0402 600/509 |
| 2008/0146276 | A1 * | 6/2008 | Lee | A61B 5/6887 455/556.1 |
| 2008/0228095 | A1 * | 9/2008 | Richardson | A61B 7/04 600/528 |
| 2008/0232605 | A1 * | 9/2008 | Bagha | A61B 7/04 381/67 |
| 2009/0099479 | A1 | 4/2009 | Solanki et al. | |
| 2012/0029308 | A1 * | 2/2012 | Paquet | A61B 5/01 600/301 |
| 2013/0018251 | A1 * | 1/2013 | Caprio | A61B 5/6832 600/393 |

FOREIGN PATENT DOCUMENTS

| | | |
|---|---|---|
| WO | 2009080040 A1 | 7/2009 |
| WO | 2010078168 A2 | 7/2010 |

* cited by examiner

MONITORING SYSTEM FOR MONITORING HEART SIGNALS

RELATED APPLICATIONS

This is a U.S. national phase application of International application no. PCT/EP2013/062467 filed Jun. 17, 2013, which claims priority to Swedish application no. 1250640-8 filed Jun. 18, 2012, and claims the benefit of U.S. provisional application No. 61/660,883 filed Jun. 18, 2012, all of which are incorporated herein by reference.

FIELD OF THE INVENTION

The present invention relates to the field of recording of heart sounds, and in particular to a monitoring system including a sensor for monitoring heart sounds and a separate, but connected monitor processor, both of which are attached to the skin of a patient.

BACKGROUND OF THE INVENTION

A widely used tool used by medical professionals for performing relative simple diagnostic tasks is the stethoscope, which is used to listen to a variety of internal body functions through the skin of a human. The conventional stethoscope is to some extent nowadays substituted by an electronic digital stethoscope which amplifies the sound captured.

The discovery of murmurs or low level noise from the coronary arteries with stenotic plaque of the beating heart was done in the 1970'ies. The plaque leads to change of the circulating blood from a laminar situation to turbulent streaming. The turbulence will lead to vibrations that may be picked up at the skin surface as sounds. In spite of the early discovery, the use of the level of intensity of the murmurs has never gained commercial impact, probably due to major challenges to make effective algorithms for the management of the sound recordings. The intensity is 100 to 1000 times less than the normal heart beat and cannot be heard by the normal ear with the stethoscope and the requirements to proper recordings are extreme. This means that any detail associated to the recording and the data management must be reconsidered for optimization or finding new solutions.

In WO-2009/080040-A1 and in WO-2010/078168-A2 a number of such aspects have been addressed. WO-2009/080040-A1 describes adhesive patches used for monitoring of acoustic signals. To enhance the quality of the recordings, the acoustic conductivity, transmission and contact between conducting means and skin surface is optimized by maintaining the pressure between the converting means and the skin surface as stable as possible. WO-2010/078168-A2 discloses an acoustic sensor assembly comprising an acoustic sensor intended to provide accurate and robust measurements of bodily sound under a variety of conditions.

In addition the following documents related topics are addressed.
US-2009/0099479 relates to an apparatus and method for determining proper endotracheal placement.
US-2008/0228095 relates to a portable viewable and audible stethoscope for visually and audibly monitoring the vital life signs of a patient.
And in U.S. Pat. No. 5,737,429 there is disclosed a multi-functional, hand-held medical device for measuring bodily functions and physiological parameters and for medical screening and diagnosis by dual sound detection.

From this point of view there is still a need for further development in the field to reach a full solution for the delicate recording of acoustic heart sounds. New equipment and methods should be developed to overcome still important issues for acquiring the best possible high quality recordings and the appropriate subsequent management thereof.

The object of the present invention is thus to provide an improved system for the recording of acoustic heart sounds.

SUMMARY OF THE INVENTION

The above-mentioned object is achieved by a monitoring system for monitoring acoustic heart signals comprising a heart sounds sensor and processor both of which are mounted to the skin of a patient with a connector disposed there between. The monitoring system comprises a sensor housing comprising a heart sound sensing element adapted to be arranged in connection to a patient's heart to sense heart sounds and to generate a heart sound signal related to the heart sounds. The system further comprises a monitoring unit housing comprising a processing unit adapted to receive the heart sound signal, wherein said monitoring unit housing is separated from said sensor housing and is adapted to be arranged in relation to the patient's upper sternum. The monitoring system further comprises a flexible elongated connector connecting the sensor housing to the monitoring unit housing, the connector having a longitudinal extension along a longitudinal axis. The connector is connected to the monitoring unit housing in an angular relationship, and the angle α between the longitudinal axis and a main axis of the monitoring unit housing is within a predetermined interval.

By separating the sensor housing from the monitoring unit housing and connecting the housings with the described flexible elongated connector, an ideal fixation of the monitoring system is achieved which to a great extent removes stresses to the sensing element derived from the monitoring unit housing. Stress between the sensor housing and monitoring housing will lead to impairment of the recording of the heart murmurs due to less precise positioning of the sensor housing and further potentially introduce external noise arising from the monitoring unit housing or due to impaired skin contact of the sensor housing.

The angular relationship between the connector and the monitoring unit housing provides a guide for a correct placement of the monitoring system on a patient. As can be seen in FIG. 1, the monitoring unit housing 4 is preferably placed fixed to the upper sternum, or breastbone, of a patient, as the upper sternum normally is relatively flat and an area of the chest mostly independent of gender, age and obesity. This area provides for a stable placement of the monitoring unit housing. The sensor housing should now be placed such as it stretches for the IC 4 position ($4^{th}$ intercostal position) on the chest above the heart. This placement enables a reliable recording of the patient's heart sounds. The IC 4 position may vary especially due to gender, age, size and obesity. The flexible and angular connection allows positioning of the sensor housing without stress induced from the monitoring unit housing. The connector ensures a stable and relatively fixed relationship between the components of the system, but at the same time provides flexibility to the monitoring system such as it can adapt to different patients with different body sizes. This design of the monitoring system provides for a high quality recording and appropriate management of the recordings and handling of the device.

Further, with appropriate selection of materials for the connector, stresses emanating from the monitoring unit housing which may introduce acoustic noise to the sensor element can be reduced. The present application thus reveals new designs of equipment to overcome still important issues for acquiring best possible high quality recordings.

Preferred embodiments are set forth in the dependent claims and in the detailed description.

SHORT DESCRIPTION OF THE APPENDED DRAWINGS

Below the invention will be described in detail with reference to the appended figures, of which:

DETAILED DESCRIPTION OF PREFERRED EMBODIMENTS OF THE INVENTION

Figure 1:
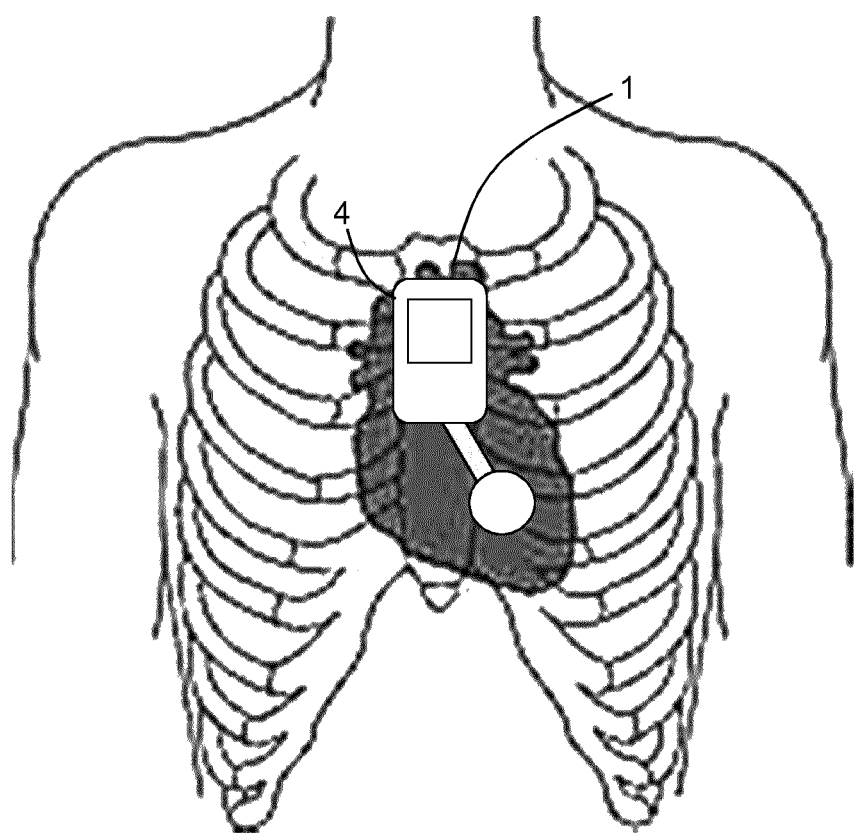
FIG. 1 illustrates a placement of a monitoring system on a patient's chest according to one embodiment of the invention.
Figure 2:
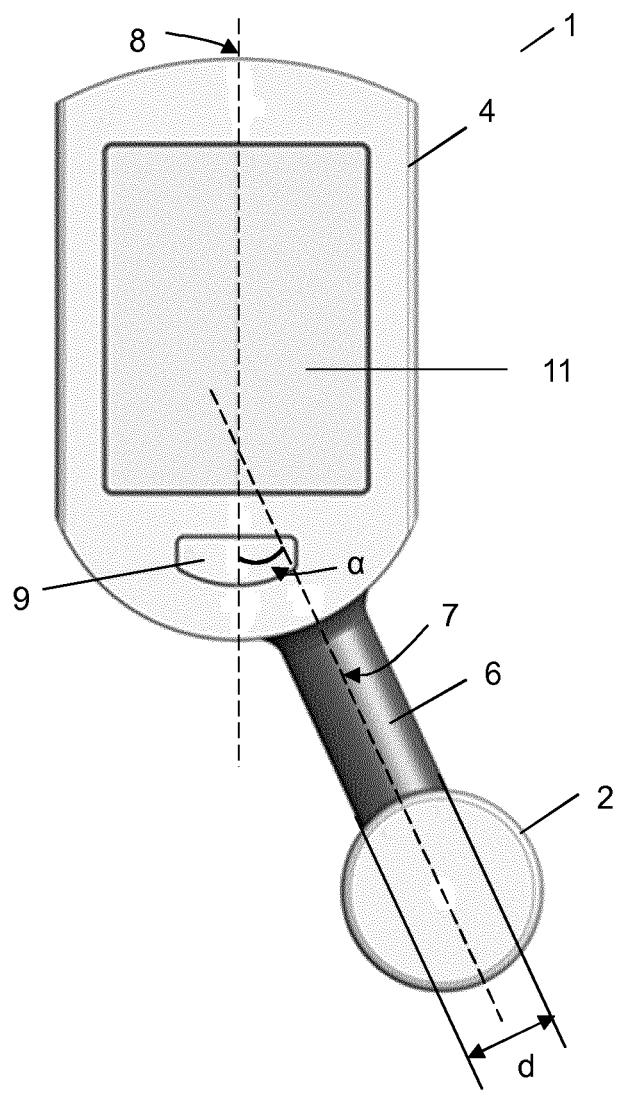
FIG. 2 shows a monitoring system according to a further embodiment of the invention.
Figure 3:
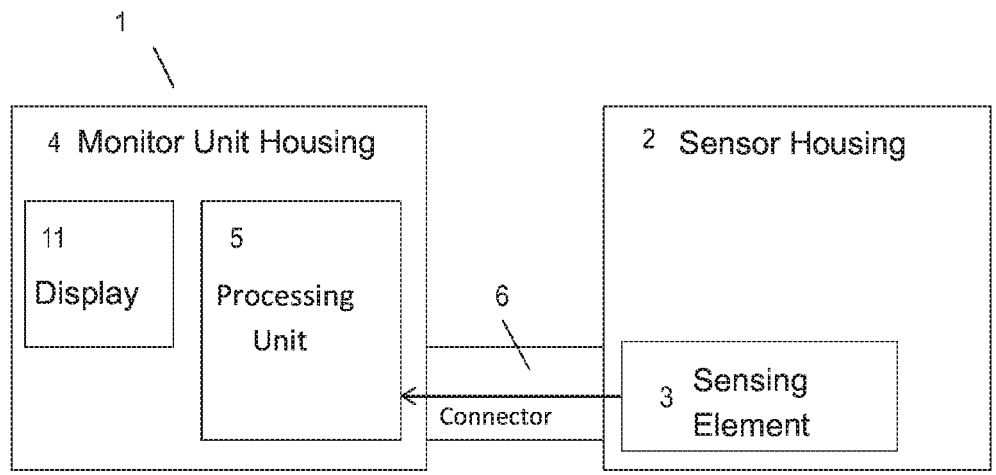
FIG. 3 shows a block diagram of the monitoring system according to a still further embodiment of the invention.

The monitoring system 1 will now be explained with reference to FIGS. 2 and 3. FIG. 2 shows the monitoring system for monitoring acoustic heart signals according to one embodiment, and FIG. 3 illustrates a block diagram of the monitoring system 1. The monitoring system 1 comprises a sensor housing 2 comprising a heart sound sensing element 3 adapted to be arranged in connection to a patient's heart to sense heart sound data and to generate a heart sound signal related to the heart sound data. The recordings by the heart sound sensing element 3 are preferably in the frequency field of 1-2000 Hz. The monitoring system 1 also comprises a monitoring unit housing 4 comprising a processing unit 5 adapted to receive the heart sound signal, wherein the monitoring unit housing 4 is separated from the sensor housing 2. The processing unit 5 is according to one embodiment accommodated in a monitoring unit (not shown). The monitoring unit is then accommodated in the monitoring unit housing 4 and further comprising at least one AD-converter to convert analogue recorded signals into digital signals, memory means and preferably a power supply such as a battery or power connection facilities to run the data management. The monitoring unit housing 4 is further adapted to be arranged in relation to the patient's upper sternum. The monitoring unit housing 4 may have a display 11 for display of data and/or a wireless communication solution for further transfer of analog or digital signals to an external unit. The external unit may e.g. be a smartphone or a computer. The digital signals are according to one embodiment processed by algorithms to make a read out value at the display showing a condition of the patient. In FIG. 2 an ON/OFF button is shown, denoted 9.

The monitoring system 1 further comprises a flexible elongated connector 6 connecting the sensor housing 2 to the monitoring unit housing 4. The connector 6 has a longitudinal extension along a longitudinal axis 7. The connector 6 is connected to the monitoring unit housing 4 in an angular relationship, and wherein the angle α between the longitudinal axis 7 and a main axis 8 of the monitoring unit housing 4 is within a predetermined interval. According to one embodiment the predetermined interval is 20-90 degrees.

The main axis 8 is an axis of the monitoring housing 4 intended to be located directly over and essentially parallel with the longitudinal extension of the breastbone of a patient when the monitoring system 1 is in use and correctly placed on a patient's chest. In the figures the monitoring unit housing 4 has a rectangular shape, and the main axis 8 is in this embodiment a centrally placed axis along the longitudinal extension of the monitoring unit housing 4. If the monitoring unit housing 4 has another shape, for example a circular shape, the monitoring unit housing 4 will in this context still have a main axis 8 which when the monitoring system 1 is in use and correctly placed, is located directly over and essentially parallel with the longitudinal extension of the breastbone of the patient. The main axis 8 is according to one embodiment denoted on the monitoring housing 4 to guide a user to a correct placement of the monitoring housing 4.

The connector 6 is preferably soft and resilient. The connector 6 is according to one embodiment characterized by connecting the monitoring unit housing 4 and the sensor housing 2 in a predetermined angle α and due to its flexible properties still allowing the positioning of the monitoring unit housing 4 and the sensor housing 2 in positions with other angles than the predetermined angle α without introducing disturbing and noise creating stresses between the monitoring unit housing 4 and the sensor housing 2.

The connector 6 is preferably easy to bend in all directions and/or to twist up to +/−45 degrees to facilitate a correct placement. To maintain the shape, the connector 6 is according to one embodiment adapted to be resiliently twisted and/or bent. Thus, the connector 6 will then return to its original shape after the recording or deformation. The connector 6 has according to one embodiment limited stretchability, to avoid major change of the distance between the housings 2, 4. The connector 6 is according to one embodiment dimensionally stable and displays shape integrity, thus the connector will essentially keep its shape. According to one embodiment, the flexible elongated connector 6 is adapted to connect the housings 2, 4 in a stable or semi-rigid but still flexible manner, such that the housings 2, 4 are constantly separated by the longitudinal extension. The expression "semi-rigid" means in this context partly or moderately rigid.

The longitudinal extension of the flexible elongated connector 6 is according to one embodiment between 10-100 mm, more preferably 25-50 mm. This length of the connector 6 is preferred as it enables a placement of the monitoring system in which good recordings of heart sounds can be achieved. The longitudinal extension of the flexible elongated connector 6 depends according to one embodiment on the chosen angle α between the monitoring unit housing 4 and the sensor housing 2. The flexible elongated connector 6 has according to one embodiment a width d of 5-50 mm, more preferably 5-20 mm. The width d of the connector 6 is shown in FIG. 2 as a distance perpendicular to the longitudinal axis 7 of the connector 6. The required flexibility of the connector 6 between the monitoring unit housing 4 and the sensor housing 2 is achieved by proper choice of dimensions and materials. For example, a connector 6 with very soft and flexible material may require larger dimensions than a connector 6 with more stiff and inflexible materials, to achieve the same stability. Preferred materials will have a low torsion modulus and have some degree of elasticity. Various types of elastomers and rubbers may be appropriate like materials having a shore A hardness preferably below 70, especially when construction thickness is more than 10-20 mm in the connection. However, preferred hardness will be shore A's below 50 and even more preferred below 40, and still even more preferred below 30. Kraton TR 1602 and TR 1101, Object Tango Black™ and Kraiburg TF 4 FMS are specific examples of suitable elastomers of the invention.

The flexibility of the connector 6 is according to one embodiment characterized by the ability to easy torsion. In clinical practice the required torsion for obtaining optimal sound recordings will be low and in general considerably lower than 45 degrees. As illustrated in example 1 below, the torque for a clinically common twisting of 15 degrees of the connector 6 in a preferred embodiment will be around 0.002 Nm. With twisting torques above 0.04 Nm at torsions of 15 degrees acting on the connector 6, the connector 6 will be too stiff to serve the purpose of applying low twisting force to the sensor housing 2 when recording the sound of the heart. Preferred embodiments of the connector 6 should thus need below 0.01 Nm in torque for twisting the connector 6 about 15 degrees.

EXAMPLE 1

The force of torsion for a preferred embodiment of the connector 6 connecting the sensor housing 2 with the monitoring unit housing 4 is described below:

The torsion is the twisting of the given object due to an applied torque measured in Nm. The torque of the connector 6 with a length of 40 mm in a preferred embodiment was determined with the equipment "Tornado bottle tester, JKM Systems" manufactured by Mecmesin. The torque is depending on angular torsion and the determinations from torsions of 15 to 90 degrees are shown in the Table 1 below.

TABLE 1

| Degree | Force/Nm |
|--------|----------|
| 15     | 0.002    |
| 30     | 0.005    |
| 45     | 0.009    |
| 90     | 0.030    |

To transfer signals between the parts of the monitoring system 1, the connector 6 comprises according to one embodiment electrical means such as leads adapted to transfer electrical signals between the sensor housing 2 and the monitoring unit housing 4. Electrical connection may also or instead be achieved with a narrow flex print circuit board with printed leads, thus an interface for transferring of a plurality of electrical signals.

Figure 4:
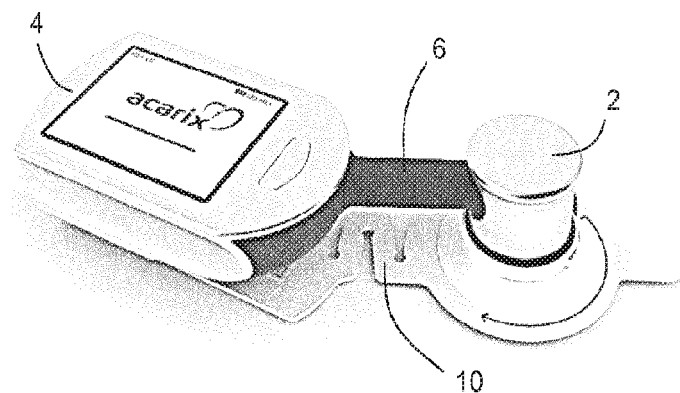
FIG. 4 shows a monitoring system according to another embodiment of the invention.

According to one embodiment shown in FIG. 4, the monitoring system comprises an adhesive patch 10 adapted to attach the sensor housing 2 and monitoring unit housing 4 to the skin of a patient. The adhesive patch 10 for the monitoring system preferably has the same angle α as between the sensor housing 2 and monitoring unit housing 4 between the intended position for the sensor housing 2 and the intended position for the monitoring unit housing 4. The patch 10 is preferably constructed from materials with high elasticity and flexibility characterized by allowing strain and twists with extremely low forces. According to one embodiment, the adhesive patch 10 comprises slits to allow non-stress movements and stretching. The construction is then cut with slits in the part which corresponds to the connector 6, to allow movement and stretching of the patch 10 without stress. Thus, when the connector 6 is twisted or bent, the patch 10 is designed such that it can follow the movement of the connector 6. Thus, attachment of the monitoring system 1 to the skin of the patient can be achieved, and still allow for flexible movement of the monitoring system 1. The patch 10 will thus not prevent movement of the monitoring system.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A monitoring system for monitoring acoustic heart signals, comprising:
    a sensor housing comprising a heart sound sensing element configured to sense heart sounds and to generate a heart sound signal related to the heart sounds sensed, wherein the sensor housing further comprises a first adhesive device by which the sensor housing is attached to the skin of a patient at a fixed position over the patient's heart;
    a monitoring unit housing comprising a processing unit adapted to receive said heart sound signal, the monitoring unit housing also comprising an integral display connected with the processing unit wherein the processing unit is programmed to process the heart sound signal and control the display to show a condition of the patient based on the processed heart sound signal, and wherein said monitoring unit housing is physically separate from said sensor housing and the monitoring unit housing further comprising a second adhesive device by which the monitoring unit housing is attached to the skin of the patient at a fixed position over the patient's upper sternum which is spaced apart from the position on the patient at which the sensor housing is attached; and
    a flexible elongated connector connecting said sensor housing to said monitoring unit housing, said connector having a longitudinal extension along a longitudinal axis, wherein said connector is connected to said monitoring unit housing in an angular relationship α, and wherein the angle α between said longitudinal axis and a main axis of said monitoring unit housing is within a predetermined interval, wherein the flexible elongated connector forms a bridge between said sensor housing to said monitoring unit housing that is spaced apart from the first and second adhesive devices and the elongated connector is adapted to be resiliently twisted and/or bent when attaching the sensor housing and the monitoring unit housing to the patient, wherein said flexible elongated connector is dimensionally stable and displays shape integrity, and wherein said flexible elongated connector is adapted to connect said housings in a stable, semi-rigid but still flexible manner, such that said housings are constantly physically separated by said longitudinal extension;
    wherein the sensor housing is configured to be connected to no more than one monitoring unit housing at a time; and
    wherein the monitoring unit housing is configured to be connected to no more than one sensor housing at a time.

2. The monitoring system according to claim 1, wherein the first and second adhesive devices are connected together to form an adhesive patch adapted to attach said sensor housing and monitoring unit housing to the skin of the patient.

3. The monitoring system according to claim 2, wherein said adhesive patch comprises slits to allow non-stress movements and stretching.

4. The monitoring system according to claim 1, wherein said predetermined interval is 20-90 degrees.

5. The monitoring system according to claim 1, wherein said longitudinal extension is between 10-100 mm.

6. The monitoring system according to claim 1, wherein said flexible elongated connector has a width of 5-50 mm.

7. The monitoring system according to claim 1, wherein said flexible elongated connector comprises a material having a shore A hardness below 70.

8. The monitoring system according to claim 1, wherein said flexible elongated connector comprises a material having a shore A hardness below 50.

9. The monitoring system according to claim 1, wherein said flexible elongated connector comprises a material having a shore A hardness below 40.

10. The monitoring system according to claim 1, wherein said flexible elongated connector comprises electrical means adapted to transfer electrical signals between said sensor housing and said monitoring unit housing.

11. The monitoring system according to claim 1, wherein the monitoring unit housing further comprises a wireless communication unit by which heart sound signals processed by the processing unit are wirelessly transmitted to an external unit.

12. A monitoring system for monitoring acoustic heart sounds, the monitoring system comprising:
a sensor housing comprising a heart sound sensing element and an adhesive patch with which to attach the sensor housing to skin of a patient at a fixed position at which the patient's heart sounds may be sensed by the sensing element, the sensing element further providing heart sound signals representative of the sensed heart sounds;
a monitoring unit housing comprising a processing unit to receive the heart sound signals from the sensing element, and an adhesive patch with which to attach the monitoring unit housing to skin at a fixed position at the patient's upper sternum which is a separate physical position from the position at which the sensor housing is attached; wherein the monitoring housing further comprises a display connected with the processing unit, wherein the processing unit is programmed to process the heart sound signals and control the display to show a condition of the patient based on the processed heart sound signal; and
an elongated connector connecting the sensor housing to the monitoring unit housing mechanically and electrically, the connector having a longitudinal extension along a longitudinal axis, wherein the connector is connected to the monitoring unit housing in an angular relationship α, wherein the angle α between said longitudinal axis and a main axis of said monitoring unit housing is within a predetermined interval, and wherein the elongated connector is formed of a material that is semi-rigid yet flexible, twistable, bendable, and stretchable, wherein the elongated connector forms a bridge between said sensor housing to said monitoring unit housing that is spaced apart from the adhesive patch and the elongated connector is adapted to be resiliently twisted and/or bent when attaching the sensor housing and the monitoring unit housing to the patient, wherein the elongated connector is dimensionally stable and displays shape integrity, and wherein the elongated connector is adapted to connect the housings in a stable, semi-rigid but still flexible manner, such that the housings are constantly separated by the longitudinal extension;
wherein the sensor housing is configured to be connected to no more than one monitoring unit housing at a time; and
wherein the monitoring unit housing is configured to be connected to no more than one sensor housing at a time.

13. The monitoring system according to claim 12, wherein a common adhesive patch is used for both the sensor housing adhesive patch and the processor housing adhesive patch, the common adhesive patch having the same angle α as the elongated connector.

14. The monitoring system according to claim 12, wherein the longitudinal extension is between 10-100 mm.

15. The monitoring system according to claim 12, wherein the elongated connector comprises a flexible printed circuit board whereby heart sound signals are electrically transferred from the heart sounds sensing element to the processing unit in the monitor housing.

16. The monitoring system according to claim 12, wherein the monitoring unit housing comprises a wireless communication unit by which heart sound signals processed by the processing unit are wirelessly transmitted to an external unit.

* * * * *